United States Patent
Lin

(10) Patent No.: US 8,506,776 B2
(45) Date of Patent: Aug. 13, 2013

(54) BIOLOGICAL TEST CHIP AND A MANUFACTURING METHOD THEREOF

(76) Inventor: Chiu-Hui Lin, Taoyuan County (TW)

( * ) Notice: Subject to any disclaimer, the term of this patent is extended or adjusted under 35 U.S.C. 154(b) by 641 days.

(21) Appl. No.: 12/715,718

(22) Filed: Mar. 2, 2010

(65) Prior Publication Data

US 2010/0219073 A1 Sep. 2, 2010

(30) Foreign Application Priority Data

Mar. 2, 2009 (TW) ................................ 98106714 A

(51) Int. Cl.
*G01N 27/327* (2006.01)
*G01N 27/26* (2006.01)

(52) U.S. Cl.
USPC .............................. 204/403.14; 204/403.11

(58) Field of Classification Search
USPC ........................................ 204/403.01–403.15
See application file for complete search history.

(56) References Cited

U.S. PATENT DOCUMENTS

| | | | |
|---|---|---|---|
| 2005/0019212 A1* | 1/2005 | Bhullar et al. | 422/56 |
| 2007/0131548 A1* | 6/2007 | Winarta et al. | 204/403.02 |
| 2007/0161070 A1* | 7/2007 | Wilsey | 435/14 |
| 2008/0006530 A1* | 1/2008 | Winarta et al. | 204/403.01 |
| 2008/0083618 A1* | 4/2008 | Neel et al. | 204/403.14 |

* cited by examiner

*Primary Examiner* — J. Christopher Ball
*Assistant Examiner* — Jennifer Dieterle
(74) *Attorney, Agent, or Firm* — Muncy, Geissler, Olds & Lowe, PLLC

(57) ABSTRACT

The present invention discloses a biological test chip and a method for manufacturing the same. The biological test chip comprises a test unit and an auxiliary unit for producing capillary action. The test unit includes a baseboard, at least one pair of electrodes and wires connected to the electrodes that are provided on the baseboard by using printed-circuit-board manufacturing process, and a photoresist layer covering the baseboard. The auxiliary unit includes a double-faced adhesive gel layer and a hydrophilic layer that have at least two thin plates respectively. By utilizing the manufacturing process for a printing circuit board and the photoresist layer, body fluid to be tested can be rapidly drawn in to fill the reaction areas formed in the photoresist layer and thereby can react evenly and rapidly with the reactive enzymes used for the test.

9 Claims, 6 Drawing Sheets

BIOLOGICAL TEST CHIP AND A MANUFACTURING METHOD THEREOF

TECHNICAL FIELD

The present invention relates to a biological test chip and a manufacturing method thereof, with simple structure and advantageous in that body fluid to be tested can be rapidly drawn in to fill the reaction areas formed in the photoresist layer and thereby can react evenly and rapidly with the reactive enzymes used for the test by utilizing the manufacturing process of a printing circuit board and the photoresist layer.

BACKGROUND

A conventional biological test chip is typically has a baseboard that is provided with a pair of detection electrodes. Reaction areas are formed in the areas containing the electrodes and are provided with reactive enzymes used for specific analysis items. After dripping a drop of body fluid to be tested in a reaction area containing a pair of electrodes to have the body fluid mixed with reactive enzyme, they will undergo electrochemical reaction. After the electrochemical reaction takes place, a corresponding signal can be produced from the electrochemical reaction and can be transferred from the pair of electrodes to another pair of electrodes via a transmission line. The another pair electrodes is electrically connected with an apparatus used for analyzing and interpreting the signal, so that analysis results of the body fluid can be obtained accordingly.

Take a test chip for blood glucose as an example, where the analysis target is blood. The test chip for blood glucose structurally comprises a base plate and other plates fastened on the base plate. The base plate of the test chip is provided with detection electrodes sensitive to an electrochemical reaction in order to detect the electrochemical reaction. One of the plates superposed on the base plate is typically a thin film provided with at least a hole. The location of the hole corresponds to the electrodes on the base plate in order to form a reaction area. Other plates are used to produce capillary action to draw the blood to be tested into the reaction area to have the blood reacted with the reactive enzyme in the reaction area.

However, the test chip is structurally disadvantageous in two aspects. First, since the electrodes and wires are typically adhered or printed on the base plate, it is difficult to put the electrodes and wires always on precisely the same locations on the base plate. Besides, when a manufacturing process is determined, it is unable to change the locations and the shapes of the electrodes or to alter the length of effective electrodes. Second, when the thin film used as the reaction area is adhered to the base plate during manufacturing process, the thin film and the base plate should be precisely aligned with each other. It is very time-consuming to perform the precise alignment. Besides, the adhesives there between may be squeezed out. If it fails to align the thin film with the base plate precisely, the electrodes that should be exposed (such as the detection electrodes or electrodes for connecting an external apparatus) may be covered thereby. Under this condition, manufactured test chips will lose their functions and become defective.

In order to overcome above shortcomings, inventor had the motive to study and develop the present invention. After hard research and development, the inventor provides a biological test chip and a manufacturing method thereof. By utilizing photoresist layer and the manufacturing process of a printing circuit board, it is advantageous in that the electrodes and wires can be more elastically and precisely arranged on a base plate, the manufacturing process can be much simplified, and the yield rate can be increased.

SUMMARY OF THE DISCLOSURE

An object of the present invention is to provide a biological test chip and a manufacturing method thereof, which are simple and utilize the manufacturing process of a printing circuit board and the photoresist layer, so that body fluid to be tested can be rapidly drawn in to fill the reaction areas formed in the photoresist layer and thereby can react evenly and rapidly with the reactive enzymes used for the test.

In order to achieve above object, the present invention provides a biological test chip comprising a test unit and an auxiliary unit. The test unit includes a baseboard, at least one pair of electrodes and wires connected to the electrodes that are provided on the baseboard, and a photoresist layer. The electrodes and wires are provided on the baseboard by using printed-circuit-board manufacturing process. The photoresist layer covers the baseboard that is provided with the electrodes and the wires. The electrodes are exposed after parts of the photoresist layer undergo exposure and development. The auxiliary unit is used for producing capillary action to draw body fluid in and includes a double-faced adhesive gel layer and a hydrophilic layer that have respectively at least one thin plate. Each plate of the double-faced adhesive gel layer is provided with an oblong recess and the bottom thereof is fastened onto the baseboard. Each plate of the hydrophilic layer is fastened to the top of one plate of the double-faced adhesive gel layer.

Moreover, the present invention also provides a method for manufacturing above biological test chip. The method comprises steps of:

A1. providing a baseboard;

A2. providing at least one pair of electrodes and wires connected to the electrodes and disposing them on the baseboard by using printed-circuit-board manufacturing process;

A3. placing a photoresist layer on the baseboard provided with the electrodes and wires connected to the electrodes;

A4. removing parts of the photoresist layer covering the electrodes and other null areas on the baseboard by means of exposure and development;

A5. adding reactive enzyme on the electrodes on the baseboard and drying it to form a test unit;

A6. providing a double-faced adhesive gel layer and a hydrophilic layer that have at least a plate respectively, where each plate of the double-faced adhesive gel layer is provided with an oblong recess; fastening each plate of the hydrophilic layer onto the top of one plate of the double-faced adhesive gel layer to form an auxiliary unit; and A7. fastening the bottom of the double-faced adhesive gel layer onto the top of the test unit precisely.

The following detailed description, given by way of examples or embodiments, will best be understood in conjunction with the accompanying drawings.

DETAILED DESCRIPTION

Figure 1:
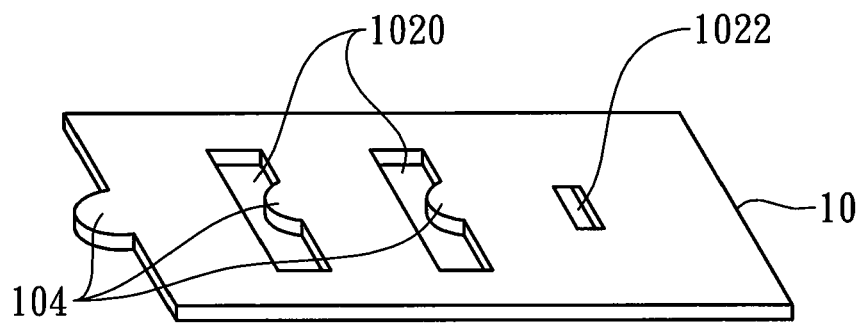
FIG. 1 shows a perspective view of a baseboard used in a first embodiment of the present invention.

The present invention discloses a biological test chip suitable for body fluid analysis. The biological test chip comprises a test unit 1 and an auxiliary unit 2. The test unit 1 includes a baseboard 10, at least one pair of electrodes 120 and wires 122 connected with the electrodes, and a photoresist layer 14.

Figure 2:
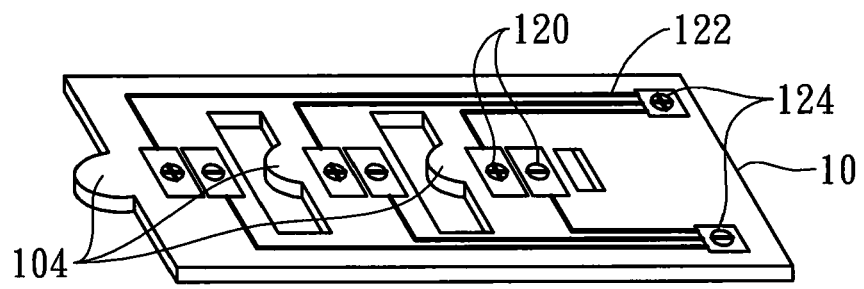
FIG. 2 is a schematic view showing that electrodes and wires are provided on the baseboard shown in FIG. 1.

Please refer to FIGS. 1 and 2 that show a first preferred embodiment of the present invention. In this embodiment, the baseboard 10 is provided with two apertures 1020 and a hole 1022 and three pairs of electrodes 120 and wires 122 connected to the electrodes are provided thereon. Three first guiding parts 104 are provided and are respectively extended from one end of the baseboard 10 and extended into the two apertures 1020. By means of printed-circuit-board manufacturing process, the electrodes 120 and wires 122 are provided on the baseboard 10 at the locations adjacent to the apertures 1020 and the hole 1022. Besides, the wires 122 of the three pairs of the electrodes 120 are extended to one end of the baseboard 10 and are connected with another pair of electrodes 124 disposed on that end. This pair of electrodes 124 is connectable with an external analysis apparatus for analyzing body fluid.

Figure 3:
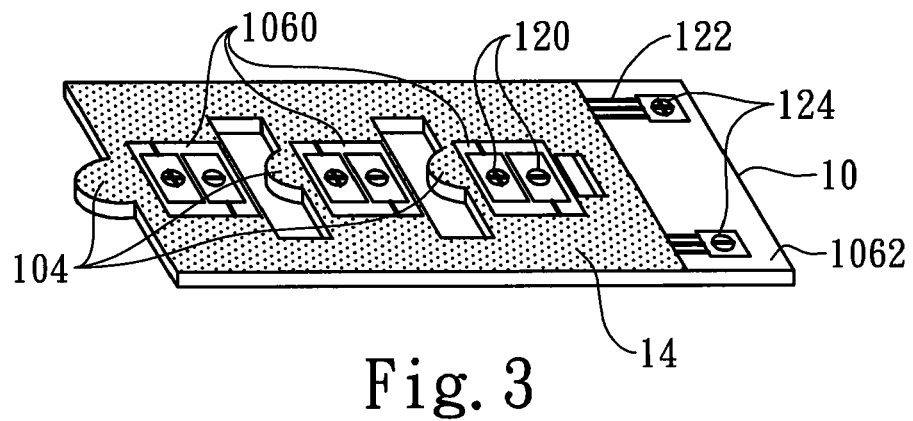
FIG. 3 is a schematic view showing that a photoresist layer is disposed on the baseboard provided with the electrodes and wires shown in FIG. 2.

The photoresist layer 14 covers parts of the baseboard 10 on which electrodes 120, 124 and wires 122 are provided. The electrodes can be exposed after parts of the photoresist layer on the baseboard 10 are removed via exposure and development. In practice, the photoresist layer is made by water-soluble acrylic resin and can be a dry film or a wet film. In this embodiment, as shown in FIG. 3, the three pairs of electrodes 120 on the baseboard 10 and another pair of electrodes 124 provided on one end thereof for connecting with an external analysis apparatus are exposed and not covered by the photoresist layer 14. The locations on the baseboard 10 on which three pairs of electrodes 120 are not covered by the photoresist layer 14 are named reaction areas 1060. Body fluid to be tested and reactive enzyme can be restricted within the reaction areas for carrying out reactions. Another location on one end of the baseboard 10 on which the pair of electrodes 124 is not covered by the photoresist layer 14 is named a null area 1062. This pair of electrodes 124 is not used to detect the signal from the electrochemical reaction of body fluid and reactive enzyme, but is connected with the wires of the three pairs of electrodes 120 for transferring the signal of the electrochemical reaction from the electrodes 120 to the external analysis apparatus.

It is advantageous to utilize the photoresist layer 14 as a limiting layer for restricting reactive enzyme therein because the thickness of photoresist layer is more uniform and better capillary action can be produced. Therefore, body fluid to be tested (such as blood) can be rapidly drawn to fill the reaction areas and thereby can react evenly and rapidly with the reactive enzyme used for the test.

The reactive enzyme for the test is dripped on the exposed electrodes 120 and then dried. After reactive enzyme is dried, it may be crystallized. However, natural crystallization of reactive enzyme is usually uneven. In this case, the crystallization of reactive enzyme can be made evenly by means of the shape of the photoresist layer since the photoresist layer in use can be placed precisely and have various patterns. Consequently, body fluid to be tested can be evenly reacted with reactive enzyme.

Figure 6:
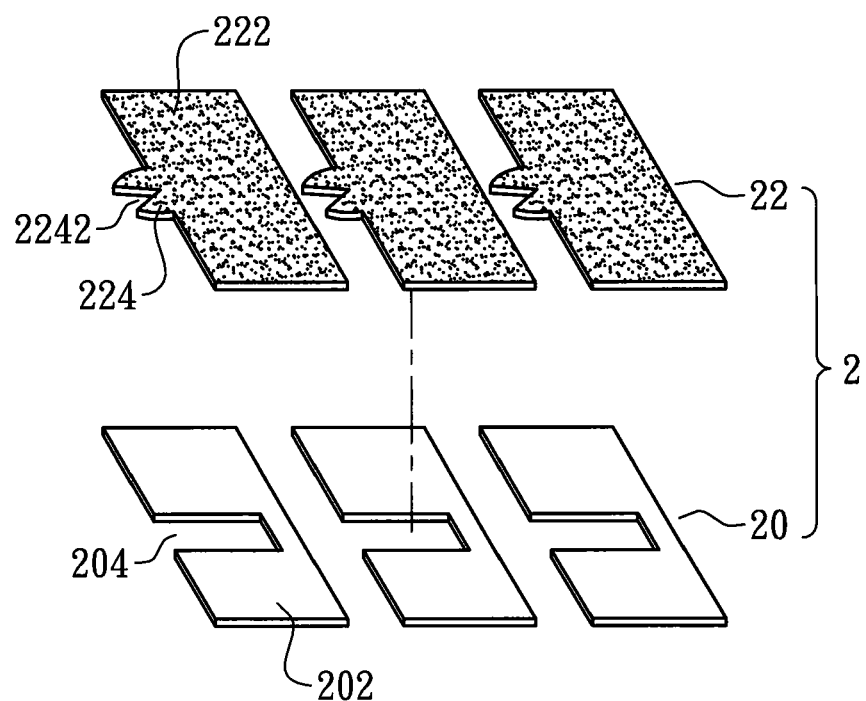
FIG. 6 shows an exploded perspective view of an auxiliary unit of the first embodiment of the present invention.

Please refer to FIG. 6. The auxiliary unit 2 includes a double-faced adhesive gel layer 20 and a hydrophilic layer 22 and is used for producing capillary action to draw body fluid into the reaction areas 1060. The adhesive gel layer 20 and the hydrophilic layer 22 respectively have at least a plate 202, 222 and the number of plates corresponds to the number of used electrodes. In this embodiment, the adhesive gel layer 20 and the hydrophilic layer 22 respectively have three separate plates 202, 222. Each plate 202 of the adhesive gel layer 20 is provided with an oblong recess 204 and is fastened onto the baseboard 10. Each plate 222 of the hydrophilic layer 22 is provided with a second guiding part 224 at one side and is fastened onto one plate 202 of the adhesive gel layer 20. Each second guiding part 224 corresponds to one first guiding part 104 and is provided with a recess 2242. In this embodiment, the recess 2242 of the second guiding part 224 is in V shape.

Moreover, the hole 1022 provided on the baseboard 10 also can be provided on the hydrophilic layer (not shown in figures) in order to achieve similar function.

In practice, the two apertures 1020 and the hole 1022 on the baseboard 10 are used to perform different functions. The hole 1022 is used for venting air while the apertures 1020 are used both for venting air and breaking part of the baseboard.

Figure 7:
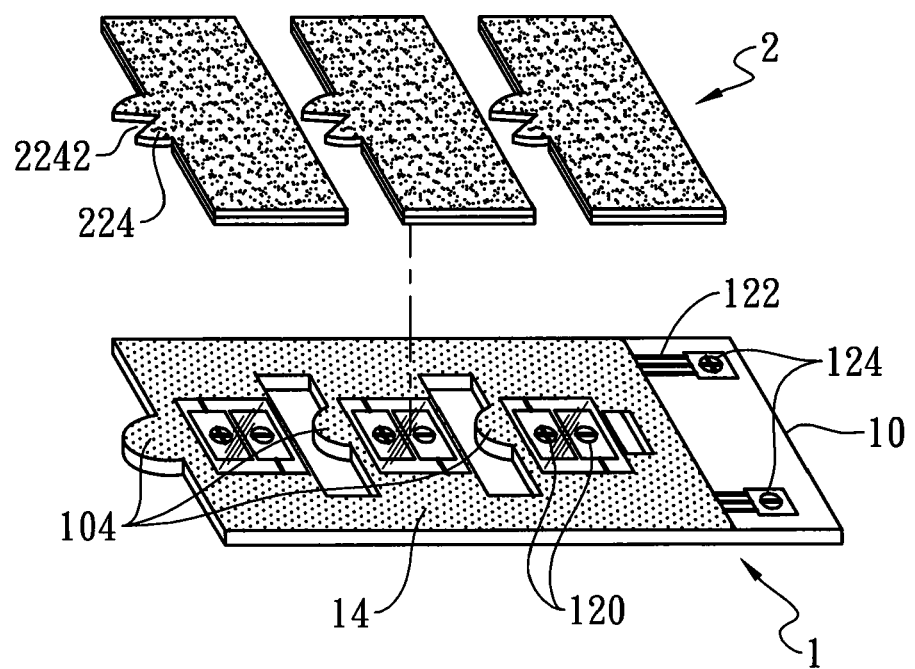
FIG. 7 is a schematic view showing that the test unit in FIG. 5 and the auxiliary unit in FIG. 6 are fastened to each other.

As shown in FIG. 7, when the auxiliary unit 2 is fastened to the test unit 1, the recess 2242 of the guiding part 224 of one plate 222 of the hydrophilic layer 22 of the auxiliary unit 2 can be used for guiding a user to drip body fluid to be tested into the recess 2242. After that, dripped body fluid can be drawn into the reaction area 1060 via the oblong recess 204 of the plate 202 of the adhesive gel layer 20 by means of the force produced by the aperture 1020. Therefore, the body fluid drawn into the reaction area 1060 can be reacted with the reactive enzyme.

Figure 8:
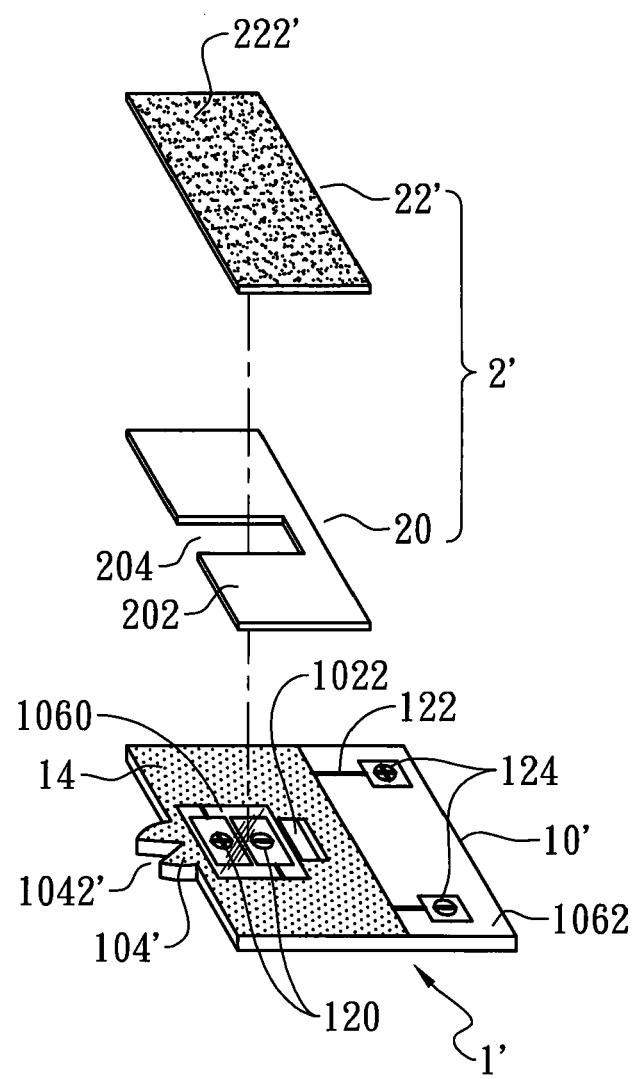
FIG. 8 shows an exploded perspective view of a biological test chip of a second embodiment of the present invention.

Please refer to FIG. 8 that shows a second preferred embodiment according to the present invention. The biological test chip in this embodiment also comprises a test unit 1' and an auxiliary unit 2'.

The test unit 1' includes a baseboard 10', one pair of electrodes 120 and wires 122 connected with the electrodes, and a photoresist layer 14. The baseboard 10' is provided with a hole 1022 and the hole 1022 simply has the function of venting air. The electrodes 120 and the wires 122 are provided on the baseboard 10' at the location adjacent to the hole 1022 by means of printed-circuit-board manufacturing process. Besides, the baseboard 10' is provided with a first guiding part 104' at one end thereof and the first guiding part 104' is provided with a recess 1042'. In this embodiment, the recess 1042' is in V shape.

Moreover, the wires 122 of the electrodes 120 are extended to another end of the baseboard 10' and connected with another pair of electrodes 124 disposed on that end. This pair of electrodes 124 is connectable with an external analysis apparatus for analyzing body fluid. The photoresist layer 14 covers the baseboard 10'. The electrodes 120 (the reaction area 1060) and the null area 1062 are exposed after parts of the photoresist layer undergo exposure and development.

The auxiliary unit 2' includes a double-faced adhesive gel layer 20 and a hydrophilic layer 22'. The adhesive gel layer 20 and the hydrophilic layer 22' respectively have one plate 202, 222'. The plate 202 of the adhesive gel layer 20 is provided with an oblong recess 204 and is fastened onto the baseboard 10'. The plate 222' of the hydrophilic layer 22' is fastened onto the plate 202 of the adhesive gel layer 20.

When the auxiliary unit 2' is fastened to the test unit 1', the hole 1022 on the baseboard 10', the oblong recess 204 of the plate 202 of the adhesive gel layer 20, and the plate 222' of the hydrophilic layer 22' can cooperate to produce capillary action. The force from the capillary action can draw the body fluid that is dripped in the recess 1042' of the first guiding part 104' into the reaction area 1062 to be reacted with reactive enzyme.

Figure 9:
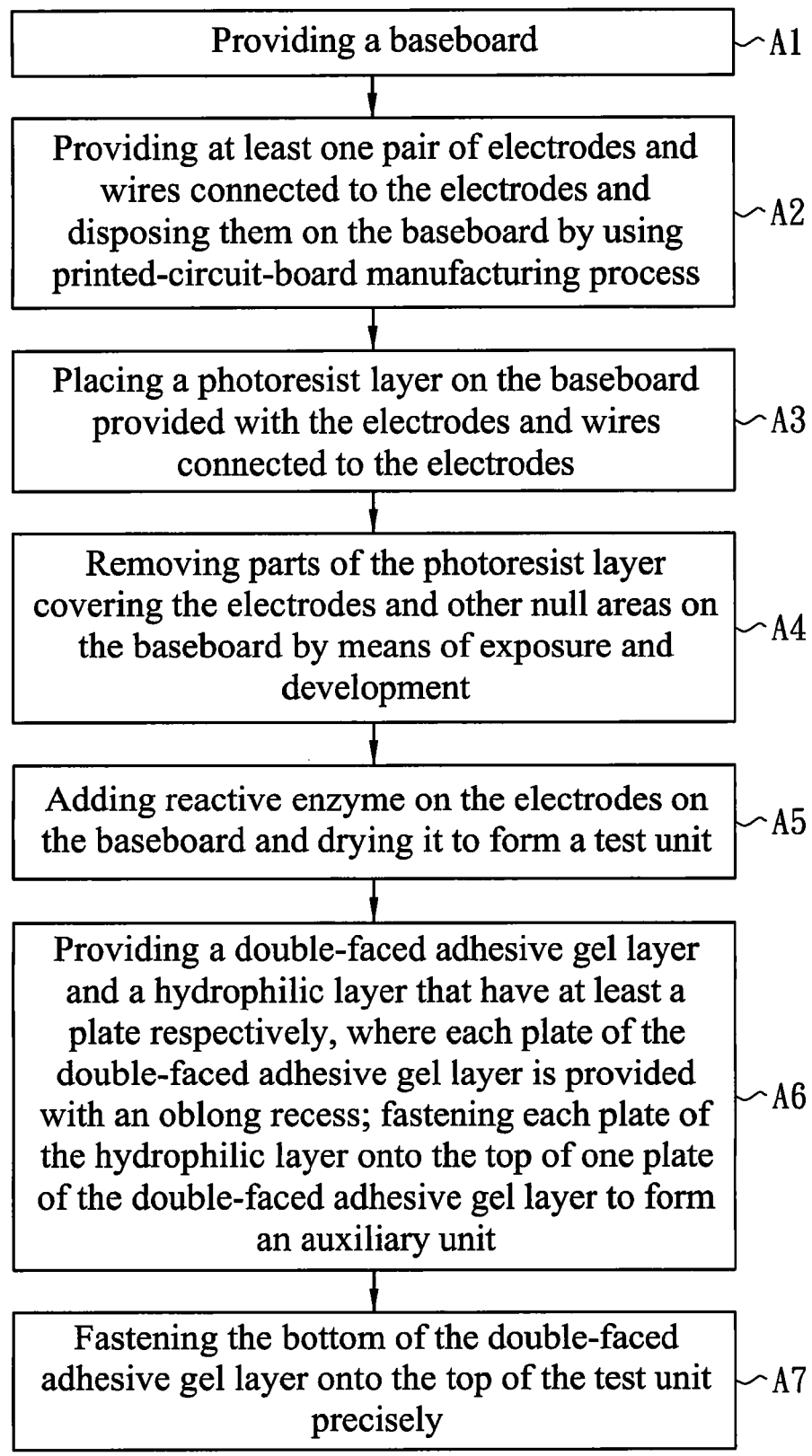
FIG. 9 shows a flowchart of a method for manufacturing a biological test chip of the present invention.

Please refer to FIG. 9 that shows a method for manufacturing a biological test chip according to the present invention. The method comprises steps of A1. providing a baseboard;

A2. providing at least one pair of electrodes and wires connected to the electrodes and disposing them on the baseboard by using printed-circuit-board manufacturing process;

A3. placing a photoresist layer on the baseboard provided with the electrodes and wires connected to the electrodes;

A4. removing parts of the photoresist layer covering the electrodes and other null areas on the baseboard by means of exposure and development;

A5. adding reactive enzyme on the electrodes on the baseboard and drying it to form a test unit;

A6. providing a double-faced adhesive gel layer and a hydrophilic layer that have at least a plate respectively, where each plate of the double-faced adhesive gel layer is provided with an oblong recess; fastening each plate of the hydrophilic layer onto the top of one plate of the double-faced adhesive gel layer to form an auxiliary unit; and A7. fastening the bottom of the double-faced adhesive gel layer onto the top of the test unit precisely.

In step A1, as shown in FIG. 1 or 8, the baseboard 10 can be provided with a hole 1022 or both of two apertures 1022 and a hole 1020. Take FIG. 1 as an example, a first guiding part 104 is extended from one end of the baseboard 10 or extended into at least an aperture.

In step A2, as shown in FIG. 2, the electrodes 120 and wires 122 are provided on the baseboard 10 by means of printed-circuit-board manufacturing process. Besides, the electrodes 120 are provided on the baseboard 10 at the locations adjacent to the apertures 1020 and the hole 1022. Besides, the wires 122 of the electrodes 120 are extended to one end of the baseboard 10 and connected with another pair of electrodes 124 disposed on that end. This pair of electrodes 124 is connectable with an external analysis apparatus for analyzing body fluid.

In practice, a further step A20 following step A2 is included: electroplating the surfaces of the wires with nickel and gold one after another.

In steps A3 and A4, first the photoresist layer 14 is coated on all the electrodes 120, 124 and wires 122 on the baseboard 10. After that, specific part of the photoresist layer 14 on the baseboard is treated with exposure and development, so that the electrodes 120 (the reaction areas 1060) and the terminal end of wires and another pair of electrodes 124 (null areas 1062) can be all exposed, that is, parts of the photoresist layer on these locations are removed.

In practice, the photoresist layer 14 is made by water-soluble acrylic resin and can be a dry film or a wet film.

Figure 4:
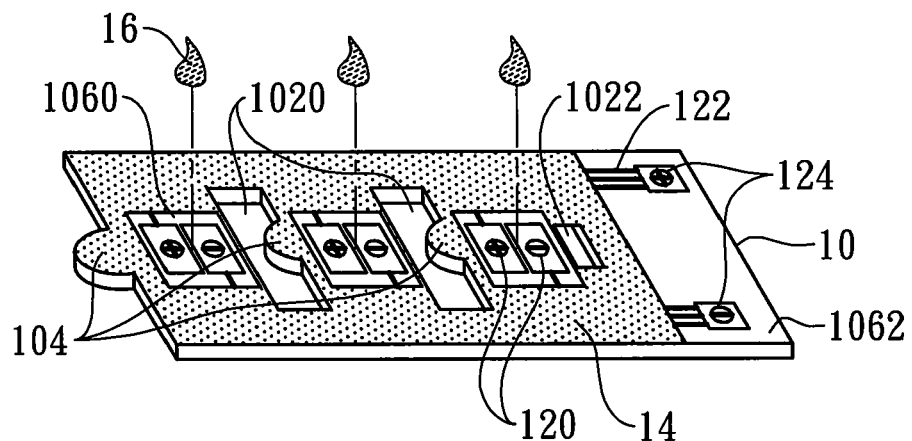
FIG. 4 is a schematic view showing that reactive enzyme is dripped onto the baseboard provided with the photoresist layer shown in FIG. 3.
Figure 5:
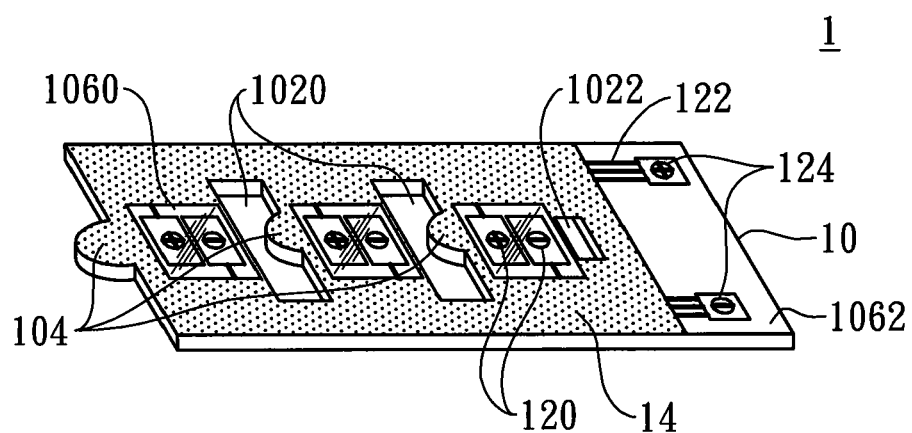
FIG. 5 shows a schematic view of a test unit of the first embodiment of the present invention.

In step A5, as shown in FIG. 4, reactive enzyme 16 is dripped onto the reaction areas 1060 and then dried. After the reactive enzyme is dried, as shown in FIG. 5, the test unit 1 is formed.

In step A6, as shown in FIG. 6, the adhesive gel layer 20 and the hydrophilic layer 22 respectively have three separate plates 202, 222. Each plate 202 of the adhesive gel layer 20 is provided with an oblong recess 204. Each plate 222 of the hydrophilic layer 22 is provided with a second guiding part 224 and the second guiding part 224 is provided with a recess 2242 that is in V shape. The second guiding part 224 is provided correspondingly to the first guiding part 104. Besides, the hole 1022 provided on the baseboard 10 also can be provided on the hydrophilic layer (not shown in figures) in order to achieve similar function.

As shown in FIG. 7, when the auxiliary unit 2 is fastened to the test unit 1, the apertures 1020 and hole 1022 on the baseboard, the plates 220 with oblong recesses 204 of the adhesive gel layer, and the plates 222 with second guiding parts 224 of the plates 222 of the hydrophilic layer 22 can cooperate to produce capillary action for drawing the body fluid to be tested into the reaction areas.

As disclosed in the above description and attached drawings, the present invention can provide an improved biological test chip and a simple manufacturing method thereof. By utilizing the manufacturing process of a printing circuit board and the photoresist layer, body fluid to be tested can be rapidly drawn to fill the reaction areas formed in the photoresist layer and thereby can react evenly and rapidly with the reactive enzyme used for the test. By precisely locating and controlling the area of the electrodes, when the electrodes are electrified, the ion speed is fast enough to improve the precision of the analysis apparatus. It is new and can be put into industrial use.

Although the embodiments of the present invention have been described in detail, many modifications and variations may be made by those skilled in the art from the teachings disclosed hereinabove. Therefore, it should be understood that any modification and variation equivalent to the spirit of the present invention be regarded to fall into the scope defined by the appended claims.

What is claimed is:

1. A biological test chip, used for body fluid analysis, comprising:
   a test unit, including:
      a baseboard, further provided with at least an aperture and at least two first guiding parts, where the guiding parts are respectively extended from one end of the baseboard and extended into each aperture;
      at least one pair of electrodes and wires connected to the electrodes that are provided on the baseboard by using printed-circuit-board manufacturing process; and
      a photoresist layer covering the baseboard that is provided with the electrodes and wires connected to the electrodes, where the electrodes are exposed after part of the photoresist layer undergoes exposure and development; and
   an auxiliary unit, used for producing capillary action to draw body fluid in, including:
      a double-faced adhesive gel layer having at least one thin plate, where each plate is provided with an oblong recess and the bottom thereof is fastened onto the baseboard; and a hydrophilic layer having at least one thin plate, where each plate is fastened to the top of one plate of the double-faced adhesive gel layer.

2. The biological test chip as claimed claim 1, wherein the baseboard is further provided with a hole.

3. The biological test chip as claimed claim 1, wherein the hydrophilic layer is further provided with at least a hole.

4. The biological test chip as claimed claim 1, wherein each first guiding part is provided with a recess.

5. The biological test chip as claimed claim 1, wherein each plate of the hydrophilic layer is provided with a second guiding part at one end, where the second guiding part corresponds to the first guiding part and has a recess.

6. The biological test chip as claimed in claim 1, wherein the photoresist layer is made by water-soluble acrylic resin.

7. The biological test chip as claimed in claim 6, wherein the photoresist layer is a dry film or a wet film.

8. The biological test chip as claimed in claim 1, wherein the exposed electrodes are provided with reactive enzyme.

9. The biological test chip as claimed in claim 1, wherein the surfaces of the wires are electroplated with nickel and gold sequentially.

\* \* \* \* \*